United States Patent
Chojin et al.

(10) Patent No.: US 8,740,898 B2
(45) Date of Patent: Jun. 3, 2014

(54) SURGICAL FORCEPS

(75) Inventors: Edward M. Chojin, Boulder, CO (US); Jessica E. C. Olson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1085 days.

(21) Appl. No.: 12/728,994

(22) Filed: Mar. 22, 2010

(65) Prior Publication Data

US 2011/0230880 A1      Sep. 22, 2011

(51) Int. Cl.
*A61B 18/14*      (2006.01)

(52) U.S. Cl.
USPC .................................. 606/45; 606/51; 606/52

(58) Field of Classification Search
USPC ................... 606/27, 28, 41, 51–52, 205–207; 607/101–102
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D348,930 S | 7/1994 | Olson |
| D384,413 S | 9/1997 | Zlock et al. |
| 5,891,142 A | 4/1999 | Eggers et al. |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D493,888 S | 8/2004 | Reschke |
| D496,997 S | 10/2004 | Dycus et al. |
| D499,181 S | 11/2004 | Dycus et al. |
| 6,837,887 B2 * | 1/2005 | Woloszko et al. ............. 606/41 |
| D509,297 S | 9/2005 | Wells |
| D525,361 S | 7/2006 | Hushka |
| 7,083,619 B2 | 8/2006 | Truckai et al. |
| 7,087,054 B2 | 8/2006 | Truckai et al. |
| D531,311 S | 10/2006 | Guerra et al. |
| D533,942 S | 12/2006 | Kerr et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 12/244,873, filed Oct. 3, 2008.

(Continued)

*Primary Examiner* — Michael Peffley
*Assistant Examiner* — Khadijeh Vahdat

(57) ABSTRACT

A forceps includes an end effector assembly. The end effector assembly includes first and second jaw members. At least one of the jaws is moveable with respect to the other between a spaced-apart position and at least one approximated position for grasping tissue therebetween. At least one of the jaw members is adapted to connect to a source of energy for sealing tissue disposed between the jaw members. A chamber is defined within and extends longitudinally along at least one of the jaw members. The chamber is configured to retain a fluid therein and includes a series of apertures disposed on a tissue-facing surface thereof such that, upon application of energy to the jaw member(s), fluid within the chamber is heated to thermally expand within the chamber and forcefully exit the apertures to divide tissue disposed between the jaw members.

1 Claim, 4 Drawing Sheets

(56) References Cited

U.S. PATENT DOCUMENTS

| | | | |
|---|---|---|---|
| D535,027 S | 1/2007 | James et al. | |
| D541,418 S | 4/2007 | Schechter et al. | |
| D541,938 S | 5/2007 | Kerr et al | |
| 7,226,448 B2 | 6/2007 | Bertolero | |
| 7,318,823 B2 | 1/2008 | Sharps et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,537,595 B2 | 5/2009 | McClurken | |
| 7,549,987 B2 | 6/2009 | Shadduck | |
| 7,604,635 B2 | 10/2009 | McClurken | |
| 7,617,005 B2 | 11/2009 | Demarais | |
| 7,620,451 B2 | 11/2009 | Demarais | |
| 7,645,277 B2 | 1/2010 | McClurken | |
| 7,651,494 B2 | 1/2010 | McClurken | |
| 7,653,438 B2 | 1/2010 | Deem | |
| 7,674,259 B2 | 3/2010 | Shadduck | |
| 7,682,305 B2 | 3/2010 | Bertolero | |
| 2001/0032002 A1* | 10/2001 | McClurken et al. | 607/103 |
| 2002/0177846 A1 | 11/2002 | Mulier et al. | |
| 2002/0198524 A1* | 12/2002 | Mulier et al. | 606/49 |
| 2005/0033278 A1 | 2/2005 | McClurken et al. | |
| 2006/0085054 A1* | 4/2006 | Zikorus et al. | 607/96 |
| 2007/0049920 A1 | 3/2007 | McClurken et al. | |
| 2009/0105703 A1 | 4/2009 | Shadduck | |
| 2009/0264879 A1 | 10/2009 | McClurken et al. | |
| 2009/0312753 A1 | 12/2009 | Shadduck | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, May 1, 2009.
U.S. Appl. No. 12/437,254, May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.

(56) References Cited

OTHER PUBLICATIONS

Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.

(56) References Cited

OTHER PUBLICATIONS

Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS

BACKGROUND

The present disclosure relates to surgical instruments. More particularly, the present disclosure relates to surgical forceps for sealing and/or dividing tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps including an end effector having first and second jaw members disposed in opposed relation relative to one another. One or both of the jaw members is moveable with respect to the other between a spaced-apart position and one or more approximated position for grasping tissue therebetween. One or both of the jaw members is adapted to connect to a source of electrosurgical energy for sealing tissue disposed between the jaw members. A chamber is defined within and extends longitudinally along one of the jaw members. The chamber is configured to retain a fluid therein and includes a series of apertures disposed on a tissue-facing surface thereof. Upon the application of electrosurgical energy to the jaw member(s), fluid disposed within the chamber is heated to thermally expand within the chamber and forcefully exit the series of apertures to divide tissue disposed between the jaw members.

In one embodiment, one or both of the jaw members includes an electrically conductive tissue sealing surface disposed on an opposed surface thereof. Each sealing surface is configured to conduct electrosurgical energy through tissue disposed between the jaw members for sealing tissue.

In another embodiment, a complementary-positioned chamber is defined within each of the jaw members. The chambers cooperate to form a complete chamber for retaining fluid on either side of tissue upon movement of the jaw members to the approximated position.

In yet another embodiment, the fluid disposed within the chamber is water.

In still another embodiment, a plurality of apertures are defined within and extend longitudinally along the tissue-facing surface of the jaw member(s).

In accordance with another embodiment of the present disclosure, a forceps is provided. The forceps includes an end effector assembly having first and second jaw members disposed in opposed relation relative to one another. One or both of the jaw members is moveable with respect to the other between a spaced apart position and one or more approximated positions for grasping tissue therebetween. One or both of the jaw members is adapted to connect to a source of electrosurgical energy. A complementary-positioned chamber is defined within each of the jaw members. The chambers cooperate to form a complete chamber extending on either side of tissue upon movement of the jaw members to the approximated position to grasp tissue therebetween. The complete chamber is configured to retain a fluid therein on either side of tissue. Upon the application of electrosurgical energy to the jaw member(s), the fluid within the complete chamber is heated to thermally expand within the complete chamber such that an internal pressure within the complete chamber is increased to a burst pressure whereby tissue disposed within the chamber is divided.

In one embodiment, the jaw members are moveable between a first approximated position for sealing tissue and a second approximated position for dividing tissue. The jaw members may be configured to apply a first clamping pressure to tissue disposed therebetween when in the first approximated position and/or may be configured to apply a second clamping pressure to tissue disposed therebetween when in the second approximated position.

In another embodiment, one (or both) of the chamber portions of the first and second jaw members includes a selectively expandable component for reducing the volume within the complete chamber. The selectively expandable component may include a shape-memory insert and/or a moveable floor.

In accordance with the present disclosure a method of sealing and dividing tissue is also provided. The method includes the steps of providing a forceps according to any of the above embodiments, positioning the jaw members such that tissue to be sealed and divided is disposed between the jaw members, moving the jaw members to the approximated position to grasp tissue disposed therebetween, and supplying electrosurgical energy to one (or both) of the jaw members to seal tissue grasped therebetween. The application of electrosurgical energy to the jaw member(s) heats the fluid within the chamber to thermally expand the fluid and divide tissue grasped between the jaw members.

BRIEF DESCRIPTION OF THE DRAWINGS

Various embodiments of the presently disclosed forceps are described herein with reference to the drawings, wherein.

DETAILED DESCRIPTION

Figure 1:
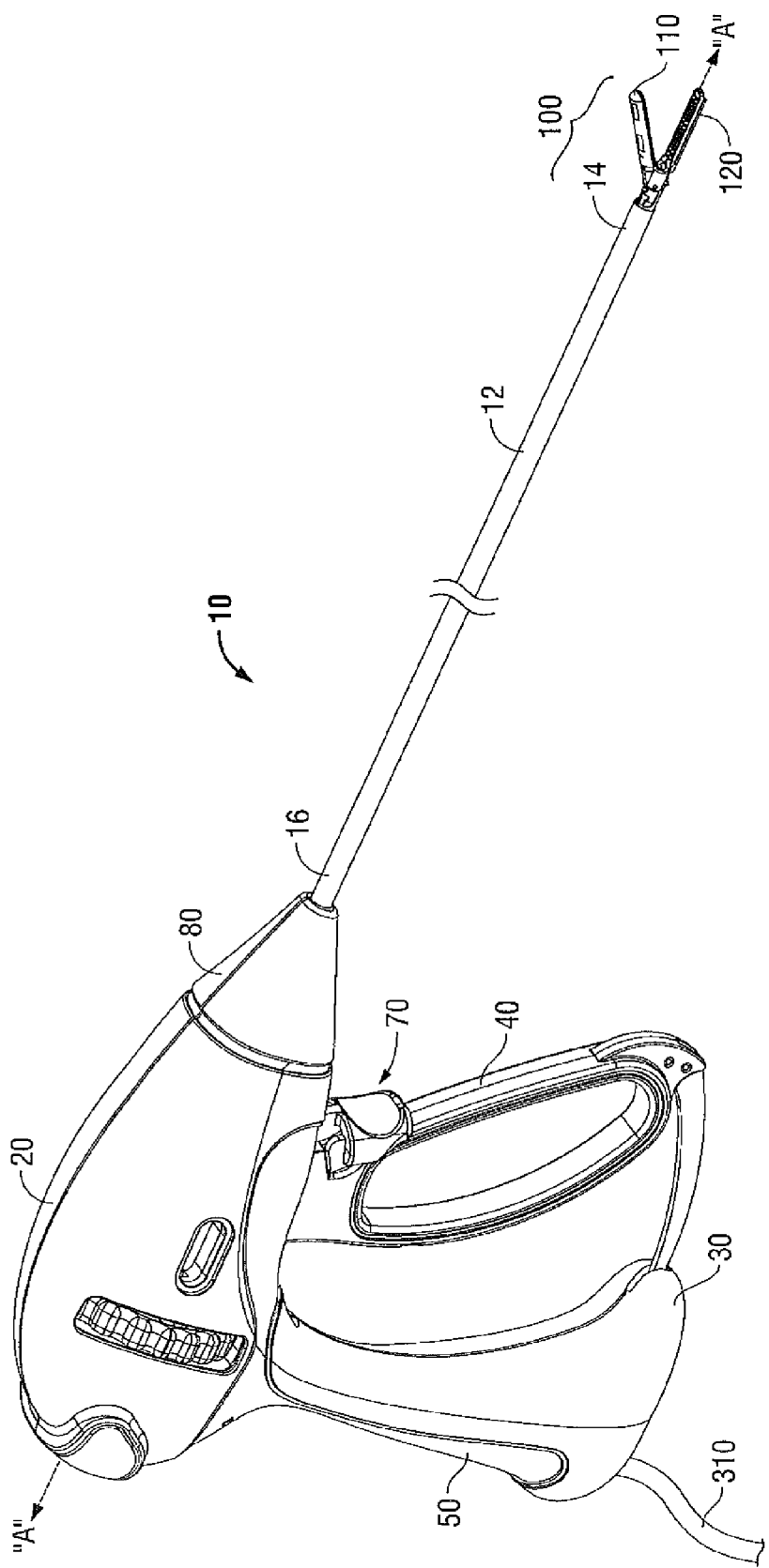
FIG. 1 is a perspective view of a forceps including an end effector assembly in accordance with an embodiment of the present disclosure.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. End effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 (FIG. 2) relative to jaw member 120. However, either, or both jaw members 110, 120 may be moveable with respect to the other. Further, although forceps 10 is shown as a laparoscopic surgical instrument, end effector assembly 100 may also be configured for use with an open surgical forceps.

Rotating assembly 80 is integrally associated with housing 20 and is rotatable approximately 180 degrees in either direction about a longitudinal axis "A," to rotate jaw members 110 and 120 with respect to housing 20.

Forceps 10 also includes electrosurgical cable 310 that connects forceps 10 to a generator (not shown). Cable 310 has sufficient length to extend through shaft 12 in order to provide electrical energy to one or both of the jaw members 110 and 120 of end effector assembly 100.

With continued reference to FIG. 1, handle assembly 30 includes a fixed handle 50 and a moveable handle 40. Fixed handle 50 is integrally associated with housing 20 and moveable handle 40 is moveable relative to fixed handle 50. Moveable handle 40 of handle assembly 30 is ultimately connected to a drive assembly (not shown) that, together, mechanically cooperate to impart movement of jaw members 110 and 120 between an open, or spaced-apart position and one or more closed, or approximated positions. For example jaw members 110, 120 may be moveable between the open position, a first approximated position for sealing tissue, and a second approximated position for dividing tissue, as will be described in greater detail below.

Figure 2:
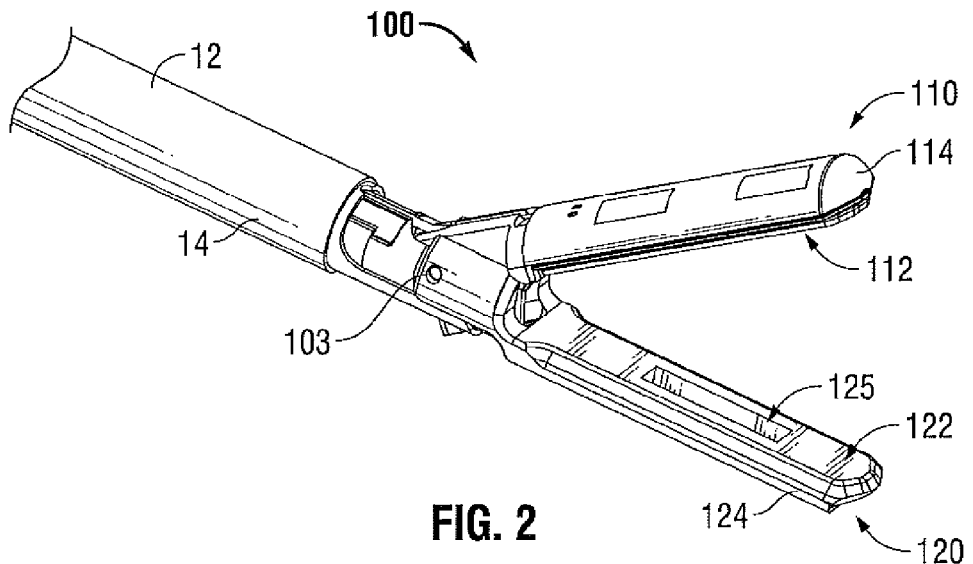
FIG. 2 is an enlarged, perspective view of an end effector assembly for use with the forceps of FIG. 1 in accordance with one embodiment of the present disclosure.

Referring now to FIG. 2, one embodiment of an end effector assembly, end effector assembly 100, configured for use with forceps 10 is shown engaged to distal end 14 of shaft 12. As mentioned above, jaw member 110 and/or jaw member 120 may be moveable with respect to the other between the open position shown in FIG. 2 and one or more approximated positions (see FIGS. 4A, 4B). Each jaw member 110, 120 includes an outer jaw housing 114, 124, respectively, and a opposed electrically conductive tissue sealing surface 112, 122, respectively. One or both of sealing surfaces 112, 122 may be adapted to connect to a source of electrosurgical energy, e.g., a generator (not shown), for conducting energy through tissue to effect a tissue seal. Accordingly, an insulated wire 140 connects each (or one of) sealing surface 112, 122 to cable 310 (FIG. 1). More specifically, insulated wire(s) 140 (FIG. 3) may be connected at a distal end thereof to sealing surfaces 112 and/or 122, thereby coupling sealing surfaces 112 and/or 122 to cable 310 (FIG. 1), which, as mentioned above, is adapted to connect to a generator (not shown).

With continued reference to FIG. 2, jaw member 120 includes a pair of sealing surfaces portions 122a, 122b disposed on either side of a chamber portion 125 that together form sealing surface 122. Chamber 125 is defined within jaw member 120 and extends longitudinally along jaw member 120 along a substantial length thereof. Chamber portion 125 generally defines a rectangular front cross-section, although other configurations are contemplated. As shown in FIG. 2, chamber portion 125 is open, or incomplete when jaw members 110, 120 are in the spaced apart position. When jaw members 110, 120 are moved to the approximated position(s), sealing surface 112 of jaw member 110 is positioned adjacent open chamber portion 125 of jaw member 120 thereby closing, or completing chamber portion 125.

Figure 3:
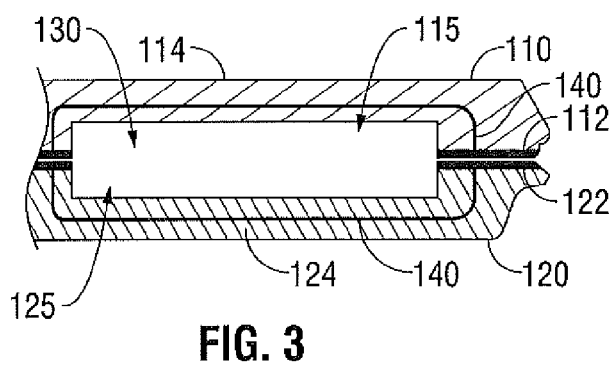
FIG. 3 is a side, cross-sectional view of the end effector assembly of FIG. 2.

Alternatively, as shown in FIG. 3, jaw member 110 may include a complementary chamber portion 115 similar to chamber portion 125 defined within jaw member 120. Chamber portion 115 of jaw member 110 is defined within and extends longitudinally along jaw member 110 between sealing surface portions 112a, 112b (collectively sealing surface 112) of jaw member 110. The open chamber portions 115, 125 of jaw members 110, 120, respectively, cooperate to form a complete, or closed chamber 130 upon approximation of jaw members 110, 120 with respect to each other. The inner surfaces of jaw members 110, 120 defining respective chamber portions 115, 125 (collectively chamber 130) may be formed from an insulating material or may be coated within an insulating material to inhibit heat from escaping the fully formed, or complete chamber 130 when jaw members 110, 120 are in the approximated position(s).

In operation, with jaw members 110, 120 disposed in the spaced apart position, end effector assembly 100 is positioned such that tissue to be sealed and/or divided is disposed between sealing surfaces 112, 122 of jaw members 110, 120, respectively. In order to better position jaw members 110, 120 of end effector assembly 100, rotating assembly 80 (FIG. 1) may be rotated with respect to housing 20, thereby rotating jaw members 110, 120 of end effector assembly 100 with respect to housing 20.

Figure 4A:
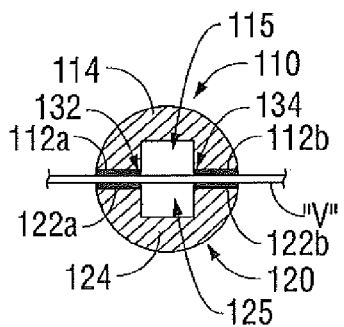
FIG. 4A is a front, cross-sectional view of the end effector assembly of FIG. 2 shown grasping tissue between first and second jaw members thereof.

With reference now to FIG. 4A, once jaw members 110, 120 are positioned with tissue disposed therebetween, moveable handle 40 (FIG. 1) may be translated, i.e., squeezed, toward fixed handle 40 to move jaw members 110, 120 from the spaced-apart position to the approximated position(s) wherein tissue is grasped between sealing surfaces 112, 122 of respective jaw members 110, 120. As mentioned above, chamber 130 is fully formed, or completed, upon movement of jaw members 110, 120 to the approximated position(s).

More particularly, when jaw members 110, 120 are moved to the first approximated position for tissue sealing, tissue, e.g., vessel "V," is grasped between sealing surface sections 112a, 122a adjacent a first side 132 of chamber 130 and between sealing surface sections 112b, 122b adjacent a second side 134 of chamber 130 with a portion of vessel "V" extending through chamber 130, as shown in FIG. 4A. In this first approximated position, jaw members 110, 120 are positioned such that a sealing, or first clamping pressure is applied to tissue grasped between sealing surfaces 112, 122.

With jaw members 110, 120 grasping tissue in the first approximated position as described above, electrosurgical energy may be applied to sealing surfaces 112, 122 of jaw members 110, 120, respectively, for sealing tissue. Upon activation, e.g., by activating a switch or trigger (not shown), insulated wire(s) 140 provides electrosurgical energy to sealing surface sections 112a and 112b of jaw member 110 (and/or to sealing surface sections 122a and 122b of jaw member 120). Electrosurgical energy is conducted through sealing surface sections 112a, 112b, through tissue, and to respective sealing surface sections 122a, 122b, of jaw member 120 to effect a tissue seal. More particularly, the portion of tissue, e.g., vessel "V," disposed between sealing surface sections 112a and 122a adjacent first side 132 of chamber 130 is sealed and the portion of vessel "V" disposed between sealing surface sections 112b and 122b adjacent second side 134 of chamber 130 is similarly sealed. In other words, vessel "V" is sealed on each side 132, 134 of chamber 130, while the portion of vessel "V" in between, i.e., the portion of vessel "V" extending through chamber 130, remains substantially unsealed.

During sealing, i.e., as electrosurgical energy is supplied to sealing surfaces 112, 122 and is conducted through tissue, sealing surfaces 112, 122 and tissue are necessarily heated. This heat generated during sealing also heats fluid disposed within chamber 130. As the fluid, e.g., air, within chamber 130 is heated, the fluid is expanded, increasing the internal pressure within chamber 130. Upon further heating, the internal pressure within chamber 130 is further increased, eventually reaching a "burst pressure." The "burst pressure" is the pressure at which the portion of vessel "V" disposed within chamber 130 bursts, or divides, due to the internal pressure within chamber 130 (see FIG. 4B).

End effector assembly 100 may be configured such that the bursting of vessel "V" (FIG. 4B) occurs simultaneously, or nearly simultaneously with tissue sealing. In other words, it is envisioned that, as electrosurgical energy is applied to sealing surfaces 112, 122 approaching the point wherein tissue disposed therebetween is adequately sealed, the internal pressure within chamber 130, due to the heating and expansion of fluid within chamber 130, approaches the "burst pressure." To this end, chamber 130, or chamber halves 115, 125, may be configured such that the "burst pressure" for a particular vessel size or particular range of vessel sizes is reached simultaneously with, or immediately after tissue sealing.

Figure 4B:
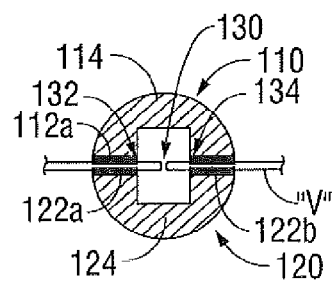
FIG. 4B is a front, cross-sectional view of the end effector assembly of FIG. 2 shown dividing tissue disposed between the jaw members.

Additionally, or alternatively, jaw members 110, 120 may be moved to a second approximated position upon the completion of tissue sealing to facilitate bursting, or dividing of tissue within chamber 130. For example, in the second approximated position, as shown in FIG. 4B, jaw members 110, 120 are approximated further with respect to one another according to a burst, or second clamping pressure. Moving jaw members 110, 120 closer together reduces the volume within chamber 130 and, correspondingly, increases the internal pressure within chamber 130. The increased pressure within chamber 130 due to the further approximation of jaw members 110, 120 may be sufficient to increase the internal pressure to the "burst pressure" and, as a result, tissue disposed within chamber 130 may burst upon movement of jaw members 110, 120 to the second approximated position. On the other hand, moving jaw members 110, 120 to the second approximated position may increase the internal pressure within chamber 130 to a point below the "burst pressure" and thus would not cause tissue therein to burst. However, increasing the internal pressure within chamber 130 even slightly reduces the amount of additional heating required to raise the internal pressure within chamber 130 to the "burst pressure," and thus facilitates tissue division.

Thus, the application of electrosurgical energy to sealing surfaces 112, 122 seals tissue on either end of chamber 130 and at or near the same time, generates heat which expands the fluid within chamber 130, increasing the pressure within internal chamber 130 to the "burst pressure" to burst, or divide tissue disposed within chamber 130. Jaw member 110, 120 may also be moved to a second approximated position to further increase the pressure within chamber 130.

Figure 8A:
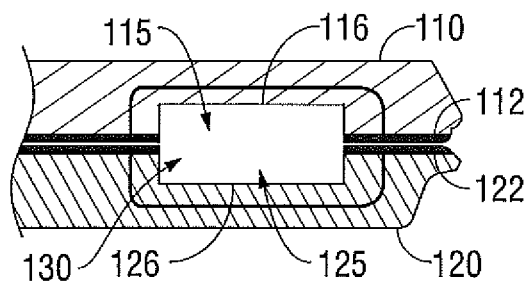
FIG. 8A is a side, cross-sectional view of the end effector assembly of FIG. 2 including an expandable insert shown in a "cold" state.
Figure 8B:
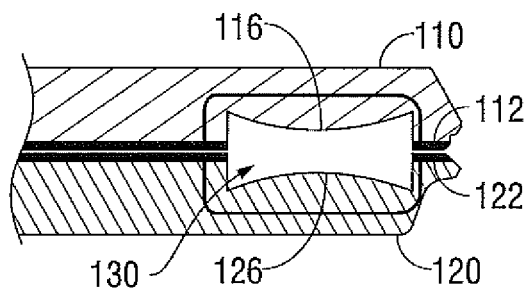
FIG. 8B is a side, cross-sectional view of the end effector assembly of FIG. 8A where the expandable insert is in a "hot" state.

Turning momentarily to FIGS. 8A-8B, the pressure within chamber 130 may be further increased by varying, e.g., decreasing, the volume within chamber 130. More specifically, chamber portion 115 and/or chamber portion 125 of jaw members 110, 120, respectively, may each include a respective temperature-dependent expandable insert 116, 126, configured to change shape when heated. Expandable inserts 116, 126 may be formed at least partially from a shape memory alloy (SMA). Suitable SMAs for forming expandable inserts 116, 126 include, but are not limited to, copper-zinc-aluminum-nickel, copper-aluminum-nickel, and nickel-titanium, commonly referred to in the art as Nitinol alloys.

Expandable inserts 116, 126 may be configured for two-way shape memory effect. Thus, expandable inserts 116, 126 of chamber portions 115, 125 of jaw members 110, 120, respectively, may be configured to remember two different shapes, a "cold" shape (e.g., an at-rest position) and a "hot" shape (e.g., an expanded position). When inserts 116, 126 are in the "cold" state, or shape, chamber 130 defines a relatively large volume, as shown in FIG. 8A. However, when inserts 116, 126 are heated to the "hot" state, or shape, as shown in FIG. 8B, the volume of chamber 130 is decreased and, thus, the pressure within chamber 130 is increased.

Further, expandable inserts 116, 126 may be configured such that heat generated during tissue sealing is sufficient to transition inserts 116, 126 from the "cold" shape (FIG. 8A) to the "hot" shape (FIG. 8B). Accordingly, bursting, or dividing of tissue disposed within chamber 130 is facilitated by the additional increase in pressure within chamber 130 due to the reduced volume of chamber 130.

Figure 9A:
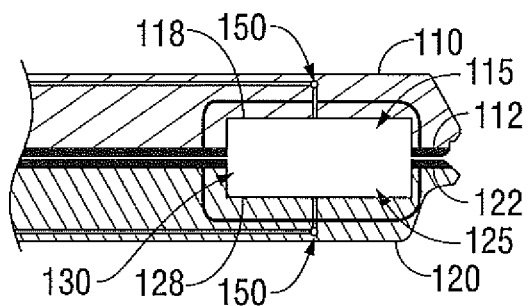
FIG. 9A is a side, cross-sectional view of the end effector assembly of FIG. 2 including a moveable floor disposed in a spaced-apart position.
Figure 9B:
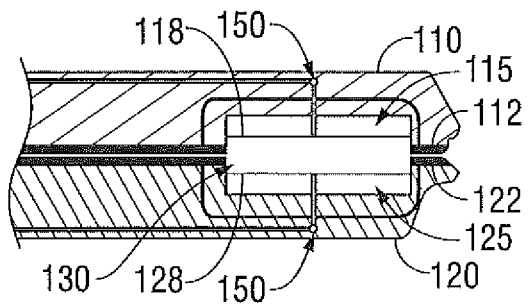
FIG. 9B is a side, cross-sectional view of the end effector assembly of FIG. 9A where the moveable floor is disposed in a closer position.

Turning now to FIGS. 9A-9B, the pressure within chamber 130 may alternatively be increased to facilitate bursting, or dividing of tissue disposed therein by mechanically reducing the volume of chamber 130. As such, one or both of chamber portions 115, 125 of jaw members 110, 120, respectively, may include moveable floors 118, 128, respectively, that are selectively translatable to decrease (or increase) the volume within chamber portion 115, 125 of jaw members 110, 120, respectively.

Accordingly, a gear assembly 150, e.g., a worm gear, may be provided for selectively translating floor 118 and/or floor 128 of chamber portions 115, 125 of jaw members 110, 120, respectively, to reduce (or increase) the volume within chamber 130. Thus, moveable floors 118, 128 may initially be disposed in a spaced-apart position, as shown in FIG. 9A, wherein chamber 130 defined a relatively large volume. However, upon activation, e.g., upon depression of a actuator (not shown) or automatically upon application of electrosurgical energy to jaw members 110, 120, gear assembly 150 translates moveable floors 118, 128 of jaw members 110, 120 toward one another, as shown in FIG. 9B, thereby reducing the volume within chamber 130, increasing the pressure within chamber 130, and, as a result, facilitating the bursting, or division of tissue disposed within chamber 130. Alternatively, any other suitable mechanism for facilitating tissue division by reducing the volume within chamber 130 to increase the pressure within chamber 130 may be provided.

Figure 5:
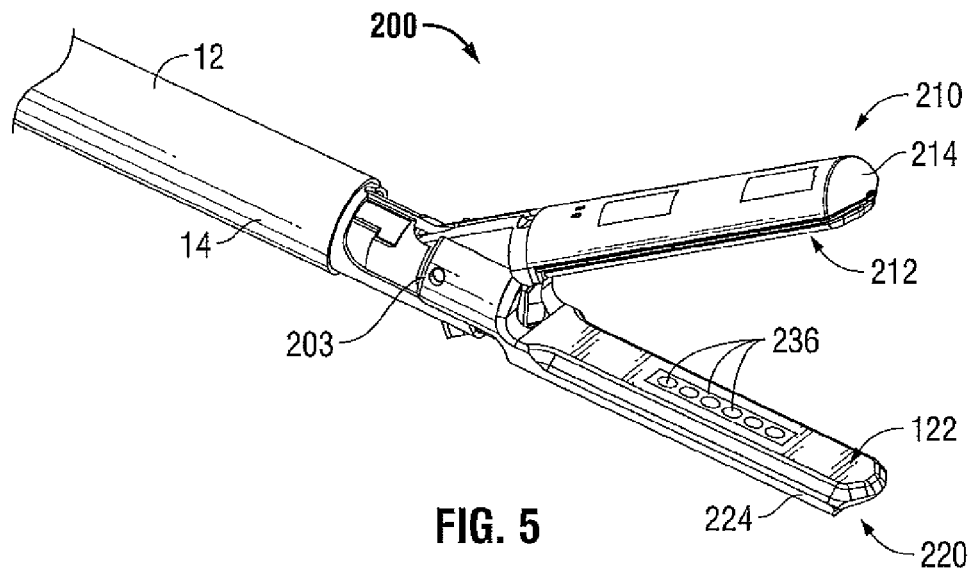
FIG. 5 is an enlarged, perspective view of an end effector assembly for use with the forceps of FIG. 1 in accordance with another embodiment of the present disclosure.
Figure 6A:
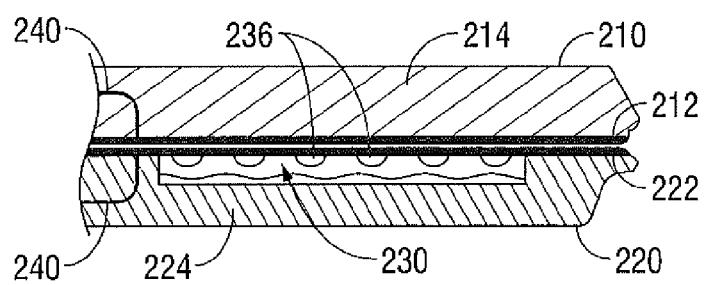
FIG. 6A is a side, cross-sectional view of the end effector assembly of FIG. 5.

Referring now to FIG. 5, another end effector assembly, end effector assembly 200, configured for use with forceps 10 is shown engaged to distal end 14 of shaft 12. Similar to end effector assembly 100, end effector assembly 200 includes first and second jaw members 210, 220 disposed in opposed relation relative to one another and pivotable about a pivot 203 between a spaced-apart position (FIG. 5) and an approximated position (FIG. 6A). Each jaw member 210, 220 further includes an outer jaw housing 214, 224 and an opposed electrically conductive tissue sealing surface 212, 222. One or both of sealing surfaces 212, 222 may be adapted to connect to a source of electrosurgical energy, e.g., a generator (not shown) via cable 310 (FIG. 1), for sealing tissue disposed between jaw members 210, 220.

Figure 6B:
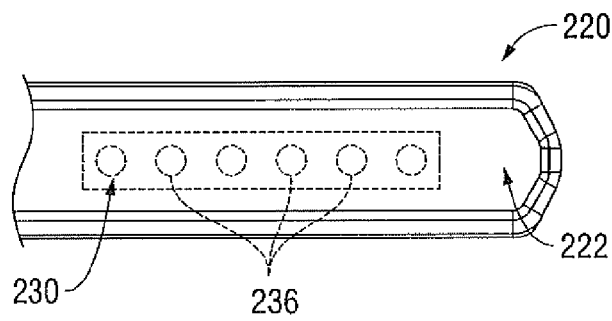
FIG. 6B is a top view of the end effector assembly of FIG. 5 wherein the top jaw member has been removed for viewing purposes.

Referring now to FIGS. 6A-6B, jaw member 220 includes an internal chamber 230 defined therein and extending longitudinally therealong. More specifically, internal chamber 230 is defined within jaw housing 224 and is enclosed by sealing surface 222 of jaw member 220. In other words, jaw housing 224 is recessed to define the side walls and floor of chamber 230, while sealing surface 222 provides a ceiling to complete, i.e., fully enclose, chamber 230. The side walls and floor of chamber 230, i.e., the portion of chamber 230 formed from jaw housing 224, may be formed from an insulating material or may be coated with an insulating material.

As shown in FIG. 6A, chamber 230 is configured to retain fluid, and more particularly, a liquid, e.g., water, therein. Accordingly, a lumen (not shown) extending through shaft 12 and into jaw member 220 may be provided to supply fluid to chamber 230, or, alternatively, chamber 230 may include a flow valve (not shown) for draining and/or filing chamber 230 with fluid. Alternatively, chamber 230 may be drained and/or filled through apertures 236 (FIG. 6B) defined within sealing surface 222.

As best shown in FIG. 6B, sealing surface 222 of jaw member 220 includes a plurality of apertures 236 defined therethrough. Apertures 236 permit fluid communication into and out of chamber 230. As mentioned above, apertures 236 may be used to drain and/or fill chamber 230 with fluid, e.g., water. Additionally, although six (6) apertures are shown, it is contemplated that more or fewer apertures 236 may be provided. Further, apertures 236 may be longitudinally-aligned in a column centered on sealing surface 222, as shown in FIGS. 5 and 6B, or may be aligned in multiple columns or in any other suitable configuration.

In preparation for use, chamber 230 is partially (or entirely) filled with fluid, e.g., water. With chamber 230 having fluid therein, end effector assembly 200 may be positioned such that tissue to be sealed and/or divided is disposed between sealing surfaces 212, 222 of jaw members 210, 220, respectively. As in the previous embodiment, rotating assembly 80 (FIG. 1) may be rotated with respect to housing 20 to better position jaw members 210, 220 with respect to tissue.

To effect tissue sealing and/or tissue division, jaw members 210, 220 are moved to the approximated position wherein tissue to be sealed, e.g., vessel "V" (FIG. 7), is grasped between sealing surfaces 212, 222. From this position, electrosurgical energy may be supplied from the electrosurgical energy source (not shown), through cable 310 (FIG. 1), through insulated wires 240, and to sealing surface 212 and/or sealing surface 222. Energy is conducted through sealing surface 212 (or sealing surface 222), through tissue, and to sealing surface 222 (or sealing surface 212) to effect a tissue seal. Accordingly, a tissue seal may be effected along a width "w" of sealing surfaces 212, 222 (FIG. 7).

During tissue sealing, i.e., while electrosurgical energy is being supplied to sealing surfaces 212, 222 and through tissue, sealing surfaces 212, 222 are necessarily heated. As a result, the fluid, e.g., water, disposed within chamber 230 is also heated during tissue sealing to vaporize water disposed within chamber 230. As such, during tissue sealing, water within chamber 230 is heated until it transitions to water vapor, or steam. As the water is converted into steam, which has a much greater volume (about 1600 times as much volume) as compared to an equal mass of liquid water, the volume of steam quickly exceeds the volume of chamber 230 and, accordingly, the steam escapes chamber 230 via apertures 236.

As mentioned above, during tissue sealing, the heated, expanding fluid within chamber 230, e.g., the liquid water being heated and transitioned to steam, escapes chamber 230 through apertures 236. The combination of a heated and expanding fluid, e.g., steam, escaping chamber 230 may be sufficient to sever, or divide, tissue positioned adjacent apertures 236. In other words, as shown in FIG. 7, as the steam is urged through apertures 236 of sealing surface 222 and into contact with vessel "V," vessel "V" is dissected partially due to thermal cutting (as a result of the heated steam) and partially due to forced dissection (as a result of the force of the expanding escaping apertures 236 and being urged through tissue clamped in place by jaw members 210, 220).

Figure 7:
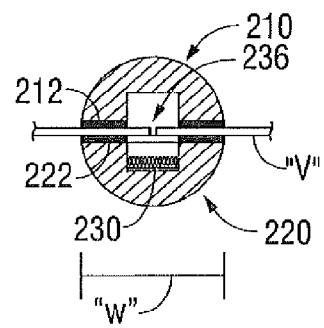
FIG. 7 is a front, cross-sectional view of the end effector assembly of FIG. 5 shown dividing tissue disposed between jaw members of the end effector assembly.

Accordingly, with apertures 236 longitudinally aligned along sealing surfaces 212, 222, the column of apertures 236 defines a "cut line." More specifically, as shown in FIG. 7, steam expanding through apertures 236 severs vessel "V" along the "cut line," which extends perpendicularly to vessel "V" and is centered with respect to the previously formed tissue seal, i.e., centered with respect to width "w" of sealing surfaces 212, 222. As an alternative to apertures 236, sealing surface 222 may include an elongated slot (not shown) defined therein. Functioning similarly to the column of apertures 236 discussed above, the slot (not shown) defines a "cut line" through which steam escapes from chamber 230 to sever tissue disposed between jaw members 210, 220. The slot (not shown) may be shaped to increase the speed of steam exiting chamber 230, e.g., via use of a Venturi. Further, although the above description is made with reference to water, other fluids that vaporize at similar temperatures to water (or at temperatures that may be reached during tissue sealing) may be disposed within chamber 230.

Thus, end effector assembly 200 is capable of sealing tissue disposed between sealing surfaces 212, 222 via the conduction of electrosurgical energy to sealing surfaces 212, 222 and through tissue and simultaneously, or near simultaneously, also provides for tissue dissecting wherein the heat generated during tissue sealing causes fluid, e.g., water, disposed within chamber 230 to be heated and expanded to a vaporous state. The hot, expanding vapor, or steam, escapes through apertures 236, severing tissue grasped between jaw members 210, 220.

In the embodiments discussed above, tissue sealing and bladeless tissue division may be effected simultaneously or near-simultaneously using a single instrument, e.g., forceps 10. Bladeless tissue division obviates the need for a cutting assembly positioned within shaft 12 or within the end effector assembly 100, 200. Eliminating the cutting mechanism simplifies the overall design, reduces the manufacturing costs of the instrument, and allows shaft 12 and/or the end effector assembly 100, 200 to define reduced diameters. Surgical instruments with reduced diameters are particularly advantageous for use in laparoscopic or endoscopic procedures wherein small incisions are provided for accessing a patient's internal tissue. More particularly, an instrument, e.g., forceps 10, having a reduced diameter may be inserted through relatively smaller incisions in tissue which allow for quicker recovery time and reduced patient discomfort. Thus, the end effector assemblies 100, 200 discussed above are particularly useful for tissue sealing and dividing during minimally invasive surgical procedures.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method of sealing and dividing tissue, comprising the steps of:
    providing a forceps including an end effector assembly disposed at a distal end thereof, the end effector assembly including first and second jaw members disposed in opposed relation relative to one another, at least one of the jaw members moveable with respect to the other between a spaced-apart position and at least one approximated position for grasping tissue therebetween, at least one of the jaw members adapted to connect to a source of electrosurgical energy, a chamber defined within and extending longitudinally along at least one of the jaw members, the chamber configured to retain a fluid therein;
    positioning the jaw members such that tissue to be sealed and divided is disposed between the jaw members;
    moving the jaw members to the approximated position to grasp tissue disposed therebetween and such that at least a portion of tissue is disposed within the chamber; and
    supplying electrosurgical energy to at least one of the jaw members such that the electrosurgical energy is conducted between the jaw members and through tissue grasped therebetween to seal tissue grasped therebetween, the application of electrosurgical energy to at least one of the jaw members heating the fluid within the chamber to thermally expand the fluid and divide the sealed tissue grasped between the jaw members.

* * * * *